(12) United States Patent
Alavi et al.

(10) Patent No.: US 10,016,461 B2
(45) Date of Patent: Jul. 10, 2018

(54) APPARATUS AND PROCESS FOR GROWING A HEART VALVE IN THREE-DIMENSIONS

(71) Applicant: The Regents of the University of California, Oakland, CA (US)

(72) Inventors: Seyedhamed Alavi, Irvine, CA (US); Arash Kheradvar, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/094,760

(22) Filed: Dec. 2, 2013

(65) Prior Publication Data

US 2014/0154662 A1 Jun. 5, 2014

Related U.S. Application Data

(60) Provisional application No. 61/732,669, filed on Dec. 3, 2012.

(51) Int. Cl.
| | |
|---|---|
| *A61K 35/34* | (2015.01) |
| *A61F 2/24* | (2006.01) |
| *A61L 27/38* | (2006.01) |
| *C12M 1/00* | (2006.01) |
| *C12M 1/12* | (2006.01) |

(52) U.S. Cl.
CPC ............ *A61K 35/34* (2013.01); *A61F 2/2415* (2013.01); *A61L 27/3804* (2013.01); *A61L 27/3808* (2013.01); *A61L 27/3826* (2013.01); *A61L 27/3886* (2013.01); *C12M 23/02* (2013.01); *C12M 23/20* (2013.01); *C12M 25/14* (2013.01); *A61L 2430/20* (2013.01)

(58) Field of Classification Search
CPC . A61K 35/34; A61L 27/3808; A61L 27/3886; A61L 27/3826; A61L 27/3804; A61L 2430/20; A61F 2/2415; C12M 23/20; C12M 25/14; C12M 23/02
USPC ................................................. 435/1.1, 289.1
See application file for complete search history.

(56) References Cited

U.S. PATENT DOCUMENTS

| | | |
|---|---|---|
| 6,666,886 B1 | 12/2003 | Tranquillo et al. |
| 6,884,621 B2 | 4/2005 | Liao et al. |
| 7,166,464 B2 | 1/2007 | McAllister et al. |
| 7,521,231 B2 | 4/2009 | Germain et al. |
| 7,851,200 B2 | 12/2010 | More |
| 7,943,353 B2 | 5/2011 | Yu et al. |
| 8,399,243 B2 | 3/2013 | Bouten et al. |
| 8,609,415 B2 | 12/2013 | Kortsmit et al. |

(Continued)

FOREIGN PATENT DOCUMENTS

| | | |
|---|---|---|
| EP | 0781116 A4 | 3/1996 |
| EP | 0847238 A1 | 12/1996 |

(Continued)

OTHER PUBLICATIONS

Katzer et al., Polyetheretherketone cytotoxicity and mutagenicity in vitro. Biomaterials, vol. 23 (2002) pp. 1749-1759.*

(Continued)

*Primary Examiner* — Kara Johnson
(74) *Attorney, Agent, or Firm* — Tope-McKay & Associates (57) ABSTRACT

The present invention relates to a heart valve and, more particularly, to a mold and process shaping and securing cells and tissue layers as they are grown in three-dimensions into a heart valve.

14 Claims, 8 Drawing Sheets

(56) References Cited

U.S. PATENT DOCUMENTS

| | | |
|---|---|---|
| 2002/0094569 A1 | 7/2002 | Yu et al. |
| 2002/0111676 A1 | 8/2002 | Bell |
| 2003/0027332 A1 | 2/2003 | Lafrance et al. |
| 2004/0121459 A1 | 6/2004 | Liao et al. |
| 2005/0069572 A1 | 3/2005 | Williams et al. |
| 2005/0095711 A1 | 5/2005 | More |
| 2005/0123520 A1* | 6/2005 | Eavey et al. ............ 424/93.7 |
| 2005/0209687 A1 | 9/2005 | Sitzmann et al. |
| 2005/0220891 A1 | 10/2005 | Yu et al. |
| 2006/0128010 A1 | 6/2006 | Germain et al. |
| 2006/0246584 A1 | 11/2006 | Covelli |
| 2006/0253192 A1 | 11/2006 | Atala et al. |
| 2006/0270028 A1 | 11/2006 | More |
| 2008/0133002 A1 | 6/2008 | Gelbart et al. |
| 2008/0145920 A1 | 6/2008 | Bouten et al. |
| 2009/0222085 A1 | 9/2009 | Kumar |
| 2009/0286278 A1 | 11/2009 | Yu et al. |
| 2011/0033885 A1 | 2/2011 | Kortsmit et al. |
| 2012/0244617 A1 | 9/2012 | Alavi et al. |
| 2013/0217128 A1 | 8/2013 | Bouten et al. |

FOREIGN PATENT DOCUMENTS

| | | | |
|---|---|---|---|
| EP | 0847238 | A4 | 12/1996 |
| EP | 1406561 | A2 | 1/2003 |
| EP | 1693025 | A1 | 8/2006 |
| EP | 2085054 | A1 | 8/2009 |
| EP | 2617389 | A1 | 7/2013 |
| WO | WO/1996/039814 | A1 | 12/1996 |
| WO | WO/2003/007795 | A2 | 1/2003 |
| WO | WO/2003/007795 | A3 | 1/2003 |
| WO | WO/2003/076564 | A2 | 9/2003 |
| WO | WO/2004/007699 | A2 | 1/2004 |
| WO | WO/2004/018008 | A1 | 3/2004 |
| WO | WO/2005/035726 | A2 | 4/2005 |
| WO | WO/2005/035726 | A3 | 4/2005 |
| WO | WO/2006/087101 | A1 | 8/2006 |
| WO | WO/2006/099334 | A2 | 9/2006 |
| WO | WO/2006/099334 | A3 | 9/2006 |
| WO | WO/2009/096780 | A1 | 8/2009 |
| WO | WO/2013/142879 | A1 | 9/2013 |

OTHER PUBLICATIONS

PCT International Search Report for PCT/US2013/072779, dated Feb. 21, 2014.

PCT Written Opinion for PCT/US2013/072779, dated Feb. 21, 2014.

\* cited by examiner

APPARATUS AND PROCESS FOR GROWING A HEART VALVE IN THREE-DIMENSIONS

CROSS-REFERENCE TO RELATED APPLICATIONS

This is a non-provisional application of U.S. Provisional Application No. 61/732,669, filed on Dec. 3, 2012, and entitled, "Apparatus for Growing a Heart Valve in Three-Dimensions."

BACKGROUND OF THE INVENTION (1) Field of Invention

The present invention relates to heart valves and, more particularly, to a mold and process for shaping and securing cells and tissue layers as they are grown in three-dimensions into a heart valve.

(2) Description of Related Art

Heart valves are integral components of vascular function and health. A healthy heart valve is required to allow blood to flow in a single direction through the various chambers of a heart. A natural heart valve may become distressed or dysfunctional for a variety of reasons, which, as can be appreciated, requires action in order for the person to maintain health and life. For example, biological or tissue valves are typically made of pig heart valves and can be surgically implanted to replace the failing natural heart valve. While functionally operable, such pig heart valves require replacement over time and are subject to rejection from the patient's body.

As such, it is desirable for heart valve replacements to more closely resemble the human heart valve and, if possible, be formed of tissue that will reduce the likelihood of bodily rejection. While it is optimal to generate a heart valve with the appropriate cell and tissue layers, generating such a valve can be problematic. Thus, a continuing need exists for an apparatus for shaping and securing cells and tissue layers as they are grown in three-dimensions into a heart valve.

SUMMARY OF INVENTION

The present invention relates to a mold and process for shaping and securing cells and tissue layers as they are grown in three-dimensions into a heart valve. For example, described is an apparatus for growing a heart valve in vitro, comprising a first part and a second part. The first part includes a heart valve-shaped protrusion with a plurality of cusps that are formed to mimic the shape of a heart valve leaflet, while the second part includes recesses that are formed to receive the heart valve-shaped protrusion.

In another aspect, at least one of the first and second parts includes an injection hole passing therethrough.

In yet another aspect, a scaffold is included for positioning between the first and second parts, the scaffold being capable of supporting three dimensional tissue formations. The scaffold is selected from a group consisting of a metal mesh and a gel/liquid solution. Additionally, as a non-limiting example, the first and second parts are formed of Polyether ether ketone (PEEK).

Additionally and in another aspect, the recesses of the second part have a tapered shape.

In yet another aspect, described is a method for growing a heart valve in vitro. The method includes several acts, such as positioning a scaffold between a first part and a second part, the first part having a heart valve-shaped protrusion with a plurality of cusps that are formed to mimic the shape of a heart valve leaflet and the second part having a recess that is formed to receive the heart valve-shaped protrusion. Thereafter, the first and second parts are closed around the scaffold such that the scaffold is enclosed within the first and second parts. A first solution of cells is introduced through an injection hole onto the scaffold. Next, the first solution of cells is incubated until a first tissue layer forms.

In another aspect, the first part is adjusted with respect to the second part to create a space around the first tissue layer. A second solution of cells is introduced through the injection hole onto the scaffold to enclose the first tissue layer. The second solution of cells is incubated until a second tissue layer forms that surrounds the first tissue layer.

In yet another aspect, the first part is adjusted with respect to the second part to create a space around the second tissue layer. A third solution of cells is introduced through the injection hole onto the scaffold to enclose the second tissue layer. The third solution of cells is incubated until a third tissue layer forms that surrounds the second tissue layer.

In another aspect, the first solution of cells includes smooth muscle cells, the second solution of cells includes fibroblast/myofibroblast cells, and the third solution of cells includes endothelial cells.

Additionally and in yet another aspect, in incubating the third solution of cells, the third tissue layer endothelializes the tissues to form a heart valve that is similar to a natural tissue.

In another aspect, the scaffold is selected from a group consisting of a metal mesh and a gel/liquid solution.

Additionally and in another aspect, the scaffold is thrilled by compressing a mesh tube between a scaffolding mold first part and a scaffolding mold second part, such that upon removal from the scaffolding mold first and second parts, the mesh tube resembles a tri-leaflet valve shape.

Finally, as can be appreciated by one in the art, the present invention also comprises a method for forming and using the invention described herein, including a heart valve formed according to the method described above and herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a heart valve and, more particularly, to a mold and process for shaping and securing cells and tissue layers as they are grown in three-dimensions into a heart valve. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and Which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Description

The present invention is directed to an apparatus (i.e., heart valve mold) and method for growing tissue-engineered heart valves in-vitro. The heart valve to be developed possesses a structure called "scaffold" capable of supporting three dimensional tissue materials. This scaffold will be combined and seeded by cells to produce biological matrix components and, finally, a naturally comparable tissue. To manufacture these tissue layers in three-dimensions (3D) using a scaffold, the present invention includes a heart valve mold to shape and secure the cells and tissue layers into the shape of a heart valve.

Figure 1:
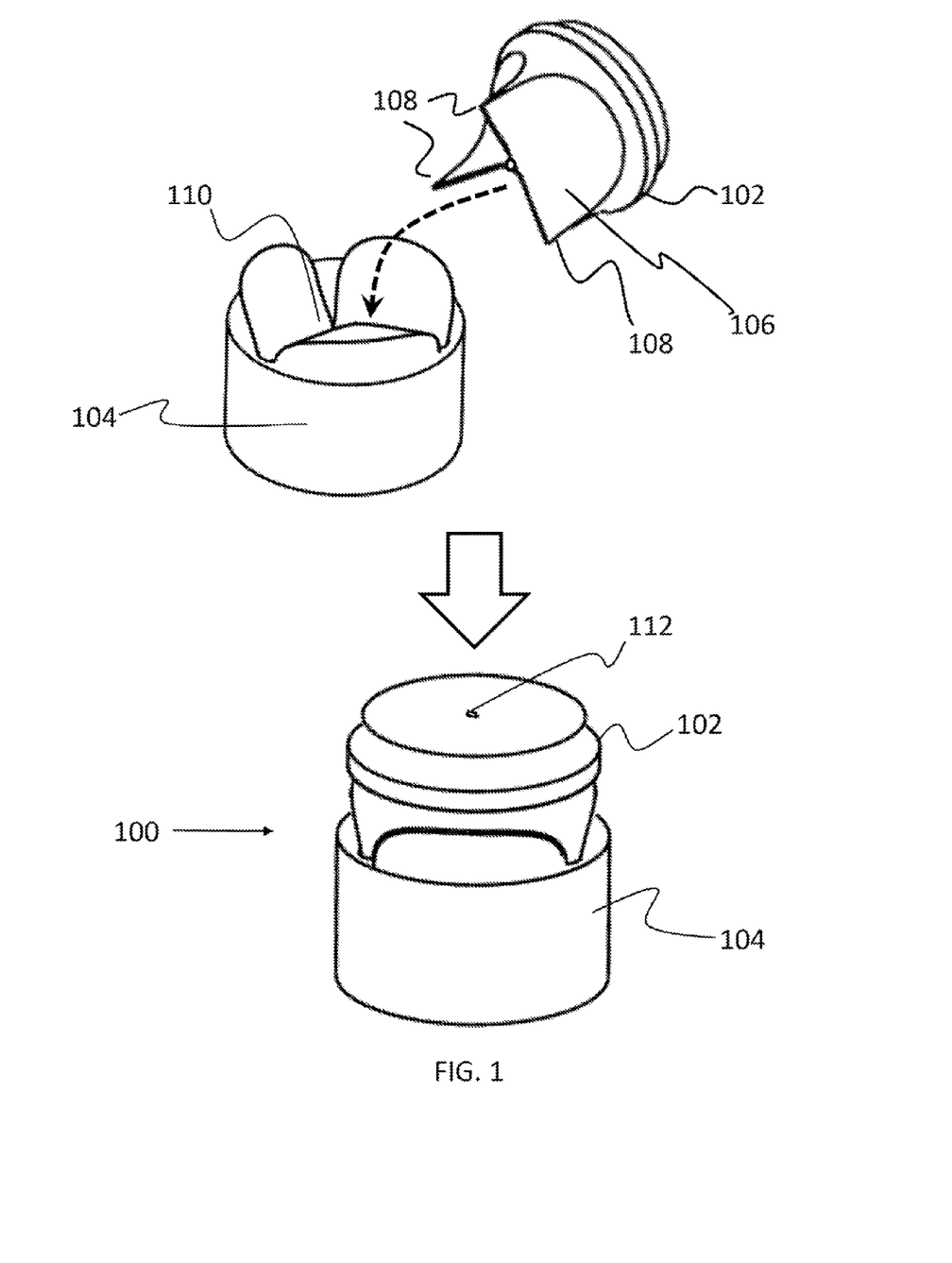
FIG. 1 is an illustration of a heart valve mold according to the principles of the present invention, depicting a first part being connected with a second part to collectively form the heart valve mold.
Figure 2A:
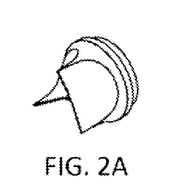
FIG. 2A is a bottom, isometric-view illustration of the first part according to the principles of the present invention.
Figure 2B:
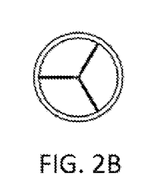
FIG. 2B is a bottom-view illustration of the first part according to the principles of the present invention.
Figure 2C:
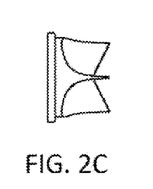
FIG. 2C is a left, side-view illustration of the first part according to the principles of the present invention.
Figure 2D:
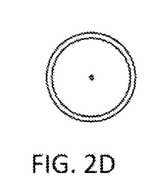
FIG. 2D is a top-view illustration of the first part according to the principles of the present invention.
Figure 2E:
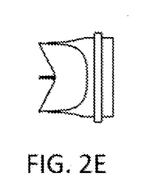
FIG. 2E is a right, side-view illustration of the first part according to the principles of the present invention.
Figure 3A:
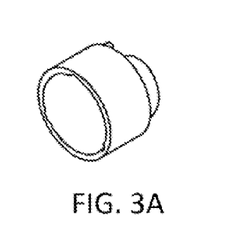
FIG. 3A is a bottom, isometric-view illustration of the second part according to the principles of the present invention.
Figure 3B:
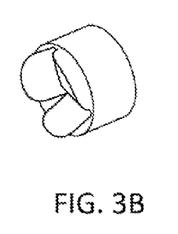
FIG. 3B is a top, isometric-view illustration of the second part according to the principles of the present invention.
Figure 3C:
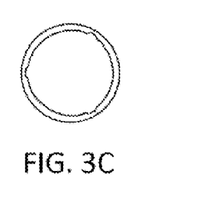
FIG. 3C is a bottom-view illustration of the second part according to the principles of the present invention.
Figure 3D:
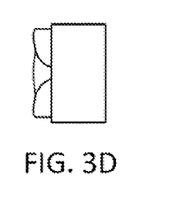
FIG. 3D is a left, side-view illustration of the second part according to the principles of the present invention.
Figure 3E:
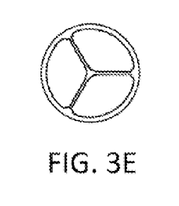
FIG. 3E is a top-view illustration of the second part according to the principles of the present invention.
Figure 3F:
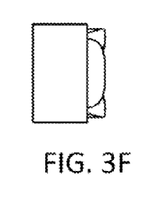
FIG. 3F is a right, side-view illustration of the second part according to the principles of the present invention.

As shown in FIG. 1, the apparatus (i.e., heart valve mold 100) includes at least two different components which secure and separate the scaffold and the cells. Specifically, the heart valve mold 100 includes a first part 102 and a second part 104 which, combined, collectively form the heart valve mold 100. The material used for the mold 100 should be biocompatible. This means that it should not secrete any chemicals harmful for the cells when it is in contact with the cells/reagents. As a non-limiting example, the first part 102 and second part 104 can be formed of be any synthetic or natural material, such as but not limited to Polyether ether ketone (PEEK).

As shown, the first part 102 includes a heart valve-shaped protrusion 106 with a plurality of cusps 108 that are formed to mimic the shape of heart valve leaflet. It should be understood that the heart valve-shaped protrusion 106 can be formed in any desired shape to generate a heart valve shape. As a non-limiting example, the heart valve-shaped protrusion 106 with its plurality of cusps 108 mimic the shape of a tri-leaflet heart valve.

The second part 104 includes a recess 110 that is formed to receive the heart valve-shaped protrusion 106 with its plurality of cusps 108. Thus and as shown, the heart valve-shaped protrusion 106 can be positioned within the recess 110 to form the heart valve mold 100.

For further understanding, FIGS. 2A through 3F illustrate several views of the first 102 and second 104 parts. Specifically, FIGS. 2A through 2E provide a bottom, isometric-view, a bottom-view, a left, side-view, a top-view, and a right, side-view illustration, respectively, of the first part 102. Alternatively, FIGS. 3A through 3F provide a bottom, isometric-view, a top, isometric-view, a bottom-view, a left, side-view, a top-view, and a right, side-view illustration, respectively, of the second part 104. Thus, as can be appreciated, the first part 102 can be connected with the second part 104 to form the heart mold 100, as depicted in FIGS. 4A through 4E. Specifically, FIGS. 4A through 4E provide a top, isometric-view, a bottom-view, a left, side-view, a top-view, and a right, side-view illustration, respectively, of the first part 102 attached with the second part 104 to form the heart valve mold 100.

Figure 4A:
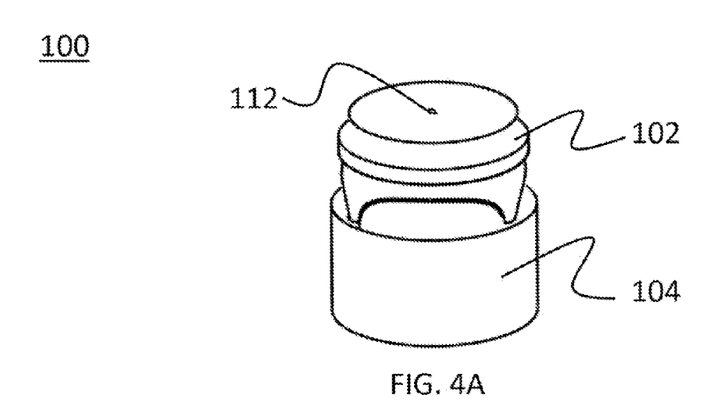
FIG. 4A is a top, isometric-view illustration of the first part attached with the second part to form the heart valve mold according to the principles of the present invention.
Figure 4B:
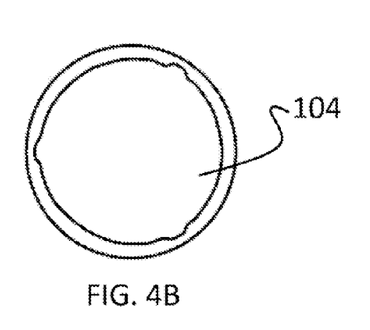
FIG. 4B is a bottom-view illustration of the heart valve mold according to the principles of the present invention.
Figure 4C:
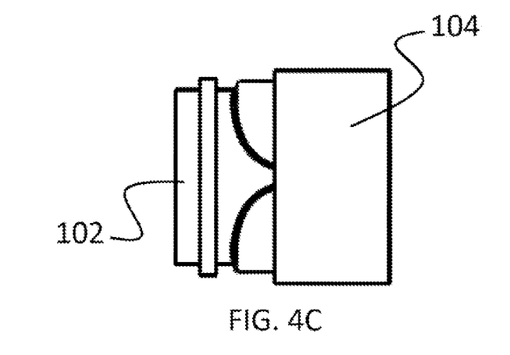
FIG. 4C is a left, side-view illustration of the heart valve mold according to the principles of the present invention.
Figure 4D:
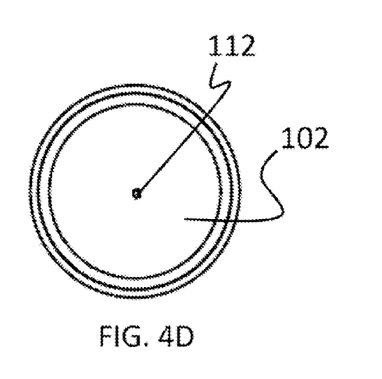
FIG. 4D is a top-view illustration of the heart valve mold according to the principles of the present invention.
Figure 4E:
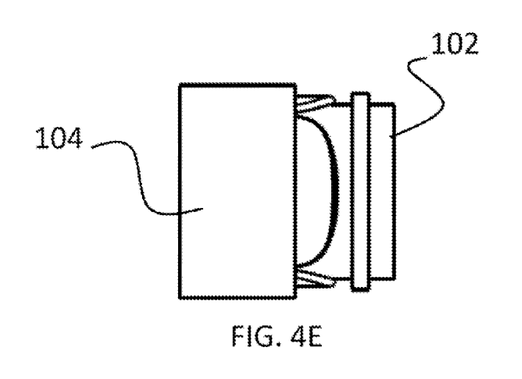
FIG. 4E is a right, side-view illustration of the heart valve mold according to the principles of the present invention.

As noted above, the heart valve mold 100 provides a shaped environment in which a user can grow tissue layers in three-dimensions (3D) to generate a heart valve. In doing so and in one aspect, the heart valve mold 100 includes an injection hole 112 (as shown in FIGS. 1, 4A, and 4D) that allows for insertion of cells or scaffolding into the mold 100. The injection hole 112 can be formed through either of the first 102 or second 104 parts for between the parts). Importantly, the injection hole 112 acts as a channel to a space between the first 102 and second 104 parts when they are connected with one another. Thus, the injection hole 112 allows a user to insert cells or material into the mold 100.

Figure 5:
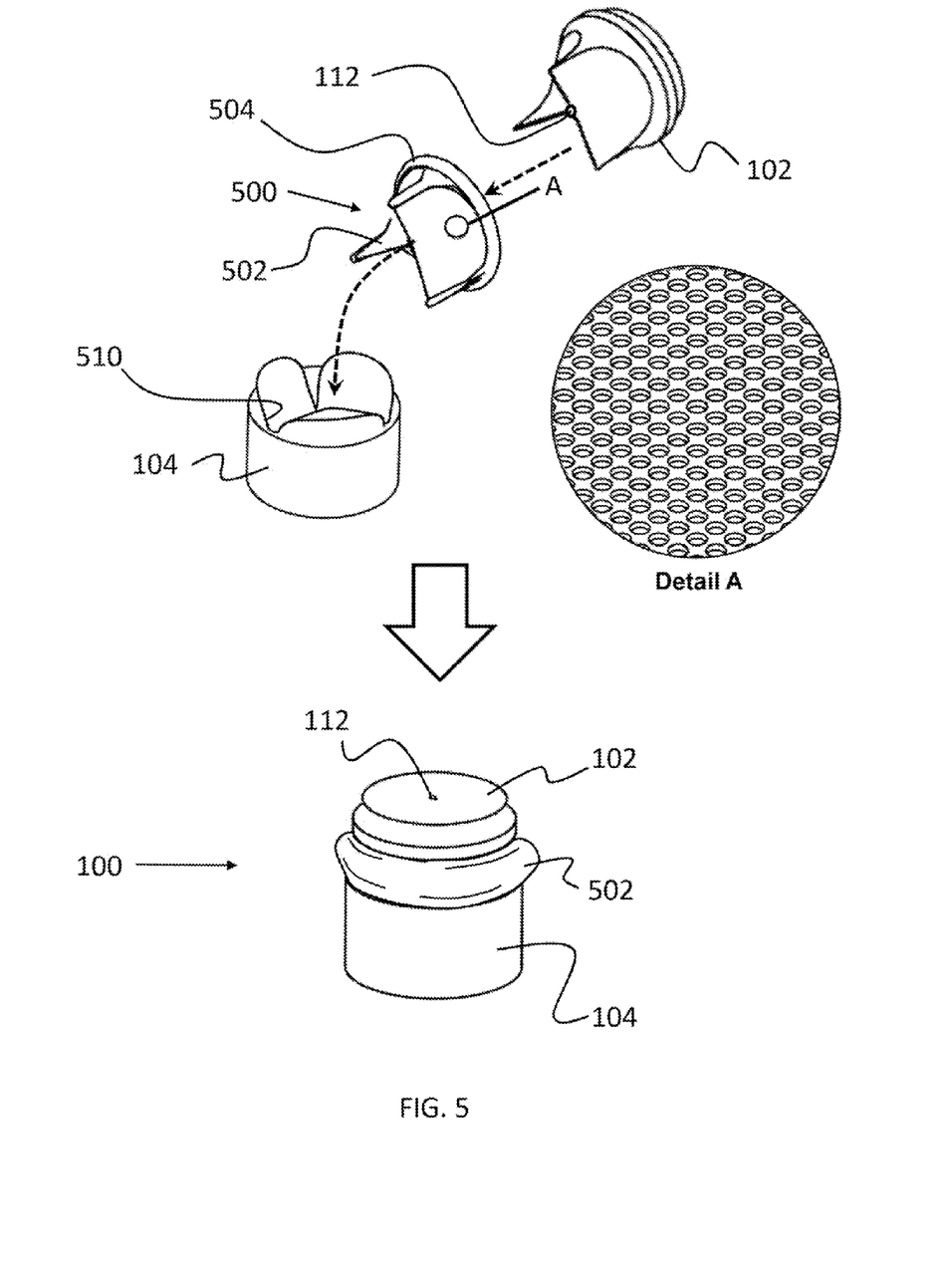
FIG. 5 is an illustration depicting a scaffold being positioned being inserted into the heart valve mold according to the principles of the present invention.

As shown in FIG. 5, to assist the growth of the cells, a scaffold 500 can be inserted into the mold 100. In other words, the scaffold 500 can be positioned and sandwiched between the first part 102 and second part 104, with the cells thereafter added through the injection hole 112 into the mold 100.

It should be understood that the first part 102 and second part 104 can be formed such that there is a hollow space inside the mold 100 to accommodate the scaffold 500 and growth or, in another aspect, formed such that no space exists.

For example, in one aspect, there is no hollow space formed between the two parts when there is no scaffold 500. However, a gap between the two parts 102 and 104 is adjustable as described below. For example, it can be increased based on the thickness of the target tissue by separating the two parts 102 and 104. In another aspect, there is always a small gap between the two parts 102 and 104. This gap is formed because the circumferential edges touch each other before the inner surfaces, so there will be a physical constraint for the female and male parts (e.g., elements 102 and 104) to completely touch each other. The type of mold 100 can be selected as desired based on the application, type of the scaffold, type of the valve, etc.

The scaffold 500 is any suitable material that can operate as a base or structure upon which the tissue layers can grow. As a non-limiting example and as depicted in FIG. 5, the scaffold can be a metal mesh 502 with holes therethrough (as shown in Detail A). In this non-limiting example, the metal mesh 502 is connected with a base ring 504 that seats around the mold 100 and fills the gap between the first 102 and second 104 parts. A specific non-limiting example of such a scaffold is described in U.S. patent application Ser. No. 13/427,807, filed on Mar. 22, 2012, and entitled, "Mesh Enclosed Tissue Constructs" which is incorporated by reference as though fully set forth herein.

It should be understood that although a mesh scaffold 500 is depicted, the invention is not intended to be limited thereto as any type of biocompatible scaffolding material can be used, including biological and polymeric scaffolding materials, such as a gel/liquid solution. A non-limiting example of such a gel/liquid solution includes synthetic polymeric scaffolds such as Polyglycolic-acid (PGA), Poly-lactic acid (PLA), Poly(lactic-co-glycolic) acid (PGLA)/PGA, PGA/Poly L, lactic acid (PLLA), Polyethylene glycol (PEG). Additional non-limiting examples of natural scaffolds that can be introduced include collagen, fibrin, hyaluronan, and small intestinal submucosa (SIS). It should be understood that any suitable biocompatible scaffold material can be used, including decellularized scaffolds and any type of matter regardless if it is degradable or not.

Figure 6:
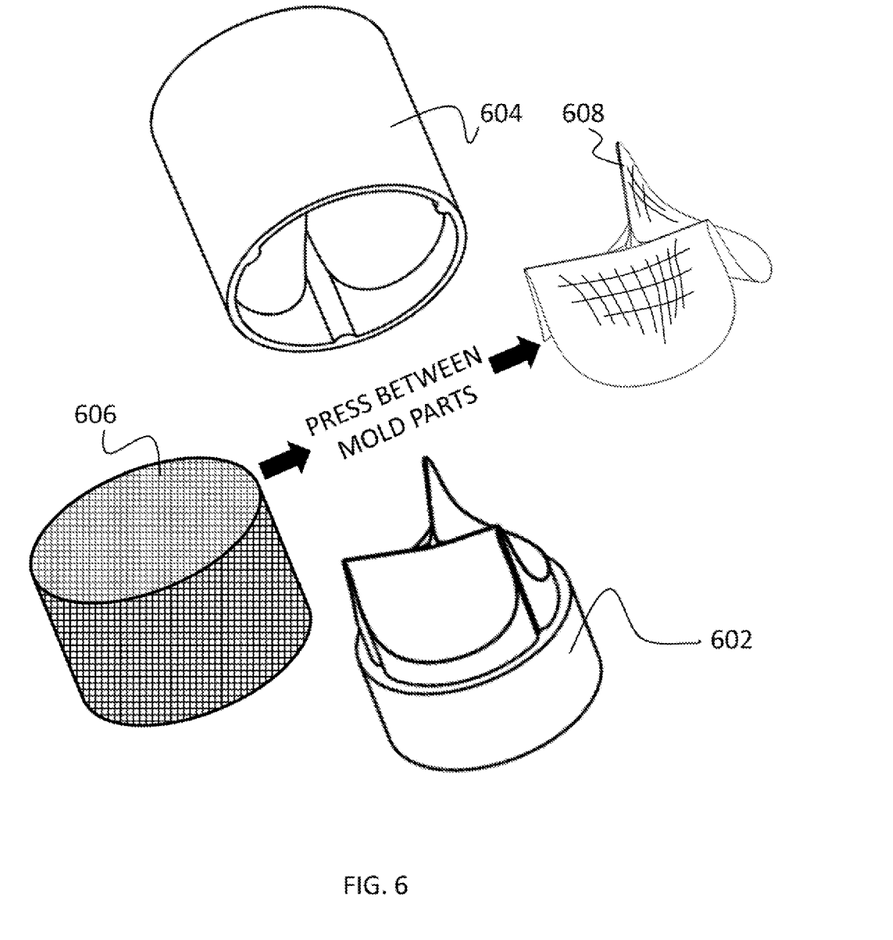
FIG. 6 is an illustration depicting a process of forming a scaffold using a scaffolding mold having a scaffolding mold first part and a scaffolding mold second part according to the principles of the present invention.
Figure 7A:
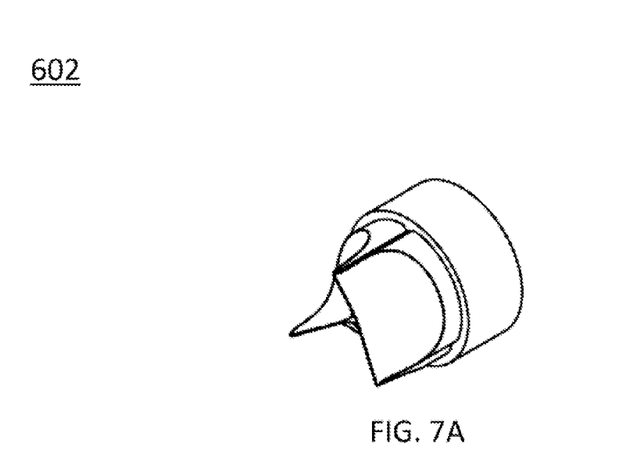
FIG. 7A is a top, isometric-view illustration of the scaffolding mold first part according to the principles of the present invention.
Figure 7B:
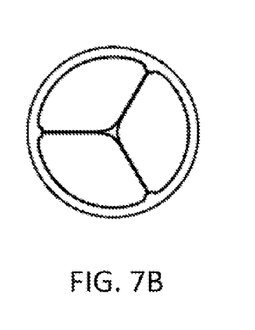
FIG. 7B is a top-view illustration of the scaffolding mold first part according to the principles of the present invention.
Figure 7C:
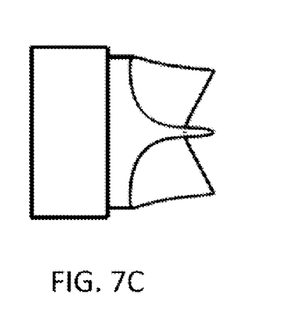
FIG. 7C is a right, side-view illustration of the scaffolding mold first part according to the principles of the present invention.
Figure 7D:
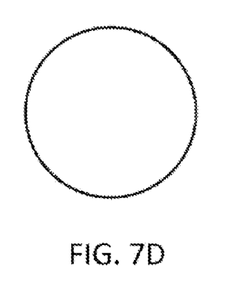
FIG. 7D is a bottom-view illustration of the scaffolding mold first part according to the principles of the present invention.
Figure 7E:
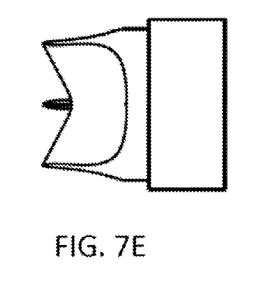
FIG. 7E is a left, side-view illustration of the scaffolding mold first part according to the principles of the present invention.
Figure 8A:
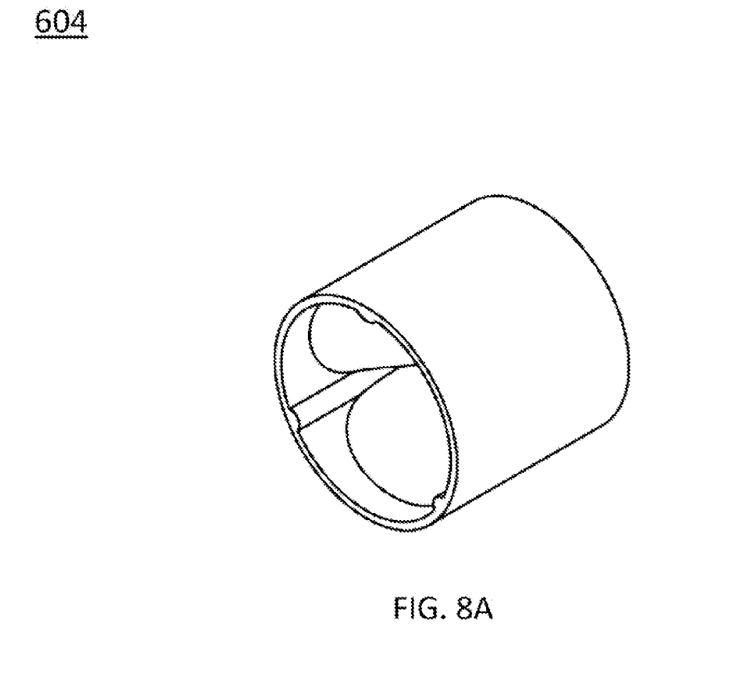
FIG. 8A is a bottom, isometric-view illustration of the scaffolding mold second part according to the principles of the present invention.
Figure 8B:
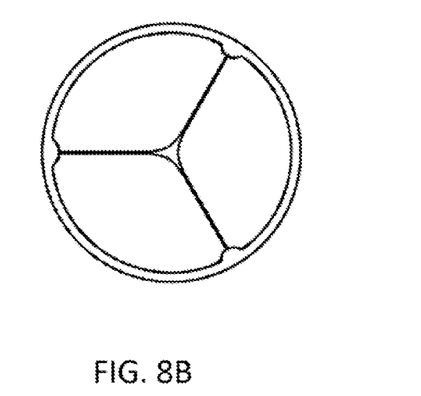
FIG. 8B is a bottom-view illustration of the scaffolding mold second part according to the principles of the present invention.
Figure 8C:
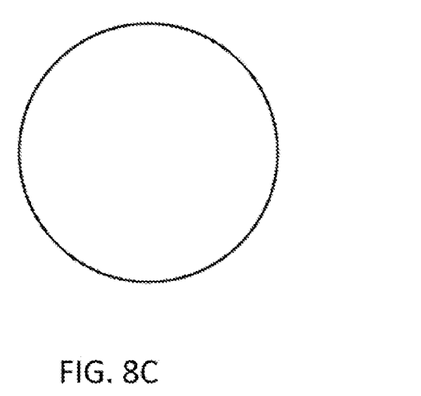
FIG. 8C is a top-view illustration of the scaffolding mold second part according to the principles of the present invention.

As yet another example, the scaffold 500 can be formed of a continuous scaffolding, meaning that the leaflets, base, and stands are all connected together and made of a single material. For example and as shown in FIG. 6, a scaffolding mold can be included that includes a scaffolding mold first part 602 and a scaffolding mold second part 604. The scaffolding mold second part 604 is formed in the shape of a desired heart valve, a non-limiting example of which includes a tri-leaflet heart valve. Alternatively, the scaffolding mold second part 604 is formed to be a negative of the shape of the scaffolding mold first part 602. Thus, when a material is positioned between the scaffolding mold first part 602 and the scaffolding mold second part 604 is pressed over and onto the scaffolding mold first part 602, the material is pressed or bent into the desired heart valve shape, thereby creating a scaffold for use with the heart mold. As a non-limiting example and as shown in FIG. 6, a braided mesh tube 606 (e.g., made of Nitinol) can be positioned over the scaffolding mold first part 602. The scaffolding mold first 602 and second 604 parts are designed in a such a way that if you put the parts 602 and 604 together, there will be a uniform gap between their surfaces so that there will be enough space for the mesh to be placed in between. Depending on the thickness of the mesh, the gap dimension can be adjusted.

Thus, the scaffolding mold second part 604 can be positioned over the metal mesh tube 606 such that the metal mesh tube 606 is pressed between the scaffolding mold first part 602 and scaffolding mold second part 604 (i.e., the two parts 604 and 606 are compressed together). In this aspect, upon removal from the scaffolding mold, the braided mesh tube 606 is pressed into the shape of a desired scaffold 608.

Referring again to FIG. 5, the scaffold 500 is positioned into the heart valve mold 100. The mold parts (i.e., first part 102 and second part 104) are then connected to each other, making it a closed structure for injection of materials via the injection hole 112. After connecting the first 102 and second 104 parts with the solid scaffold 500 in between, the cells (with or without their biological matrix) can be injected into the mold 100. As noted above, to seed the cells into/onto the scaffold 500 (or in the case in which the scaffold is in liquid/gel shape), the injection hole 112 allows the cells/scaffold to be injected into the heart valve mold 100. Depending on the type of scaffold 500, the mold 100 with its components should be placed for a certain period of time into a standard incubator at a suitable temperature and with a suitable gas ratio. As a non-limiting example and for illustrative purposes only, for example, if the scaffold is made of collagen and there is only one type of cells such as fibroblast cells, this time is about 4 to 10 days for the tissue to form. Further, as a non-limiting example, the incubator can be maintained at 37° C. with 5% $CO_2$. The liquid/gel/solid scaffold 500 with the cells inside it is going to be casted (grown in 3D) into the shape of a heart valve.

The mold has the ability to adjust the space between its two different components (i.e., first part 102 and second part 104) so that multiple types of cells and tissue layers can be added at different steps. This has been achieved by providing a tapered shape 510 for the side cavities of the bottom part (i.e., second part 104). Therefore, the first layer of tissue can be formed by injecting the cells (either with the scaffold 500 inside the mold 100 or when the cells are mixed with the scaffold (via a liquid/gel scaffold)) into the mold 100. As a non-limiting example, the first layer includes smooth muscle cells that are injected into the mold 100.

The mold 100 should be placed in an incubator as described and the cells should be fed using a proper media for a certain period of time until the first tissue layer forms. As a non-limiting example, the basal media for culturing cells contain DMEM (e.g., Dulbecco's Modified Eagle Medium, Gibco, produced by Invitrogen Corporation, located at 1600 Faraday Ave., Carlsbad, Calif. 92006, USA), 10% fetal bovine serum (HyClone, Rockford, Ill.), 1% penicillin/streptomycin (Gibco, Carlsbad, Calif.) and 1% L-glutamine (Gibco, Carlsbad, Calif.), with appropriate growth factors added to it for enhancement of growth and proliferation.

Then, after the first layer is formed, in another step, the space between the first 102 and second 104 parts of the mold 100 can be adjusted again to have enough space for the addition of the second layer. Such an adjustment can occur by simply separating the first part 102 a little from the second part 104, thereby increasing the space between the first 102 and second 104 parts. Thereafter, a second layer can be injected into the mold to enclose the first layer and form a tissue around it. A non-limiting example of such a second layer includes fibroblast/myofibroblast cells.

Additionally, a third layer (such as but not limited to endothelial cells) can also be subsequently added in a similar manner. This third layer will endothelialize the valve to make it similar to a natural tissue and will produce enough extracellular matrix components, such as but not limited to collagen, elastin and glycosaminoglycan.

When the desired cell layers have been added and the predetermined period is over, the manufactured bean valve should be removed from the mold 100 carefully so that appropriate media and supplements can be added to it later. As can be appreciated by those skilled in the art, the steps that need to be taken after are quiet similar to the conventional cell culture techniques. For example, the steps include but are not limited to changing the media every two to three days, adding growth factors such as TGF-β1, dynamic conditioning of the valve by using a bioreactor for few hours a day for 3 to 14 days, using perfusion bioreactors, and generally increasing the amount of extracellular matrix proteins by either a mechanical or chemical signal. When the valve is mature enough (about one to two months) it is ready for implantation in-vivo.

What is claimed is:

1. An apparatus for growing a heart valve in vitro, comprising:
    a first part, the first part having a heart valve-shaped protrusion with a plurality of cusps that are formed to mimic the shape of a heart valve leaflet;
    a second part, the second part having recesses and integrally formed surrounding sidewalls, the recesses being formed to receive the heart valve-shaped protrusion, where the recesses are laterally enclosed by the integrally formed surrounding sidewalls, thereby eliminating lateral access to the recesses; and
    wherein at least one of the first and second parts includes an injection hole passing therethrough.

2. The apparatus as set forth in claim 1, wherein the injection hole is centrally disposed such that material passing through the injection hole is deposited at an intersection of the plurality of cusps.

3. The apparatus as set forth in claim 2, further comprising a scaffold for positioning between the first and second parts, the scaffold being capable of supporting three dimensional tissue formations.

4. The apparatus as set forth in claim 3, wherein the scaffold is selected from a group consisting of a metal mesh and a gel/liquid solution.

5. The apparatus as set forth in claim 4, wherein the first and second parts are formed of Polyether ether ketone (PEEK).

6. The apparatus as set forth in claim 5, wherein the recesses of the second part have a tapered shape.

7. A method for growing a heart valve in vitro, comprising acts of:
    positioning a scaffold between a first part and a second part, the first part having a heart valve-shaped protrusion with a plurality of cusps that are formed to mimic the shape of a heart valve leaflet and the second part having a recess and integrally formed surrounding sidewalls, such that the recess is surrounded and laterally enclosed by the integrally formed surrounding sidewalls, thereby eliminating lateral access to the recess, the recess formed to receive the heart valve-shaped protrusion;
    closing the first and second parts around the scaffold such that the scaffold is enclosed within the first and second parts;
    introducing a first solution of cells, through an injection hole, onto the scaffold;
    incubating the first solution of cells until a first tissue layer forms;
    adjusting the first part with respect to the second part to create a space around the first tissue layer;
    introducing a second solution of cells, through the injection hole: and
    incubating the second solution of cells until a second tissue layer forms that surrounds the first tissue layer.

8. The method as set forth claim 7, wherein in introducing a first solution of cells, through an injection hole, the cells are introduced to an intersection of the plurality of cusps; and wherein in introducing a second solution of cells, through the injection hole, the cells are introduced through the injection hole to an intersection of the plurality of cusps.

9. The method as set forth in claim 7, further comprising acts of:
    adjusting the first part with respect to the second part to create a space around the second tissue layer;
    introducing a third solution of cells, through the injection hole to an intersection of the plurality of cusps, onto the scaffold to enclose the second tissue layer; and
    incubating the third solution of cells until a third tissue layer forms that surrounds the second tissue layer.

10. The method as set forth in claim 9, wherein the first solution of cells includes smooth muscle cells, the second solution of cells includes fibroblast/myofibroblast cells, and the third solution of cells includes endothelial cells.

11. The method as set forth in claim 10, wherein in incubating the third solution of cells, the third tissue layer endothelializes the tissues to form a heart valve that is similar to a natural tissue.

12. The method as set forth in claim 11, wherein the scaffold is selected from a group consisting of a metal mesh and a gel/liquid solution.

13. The method as set forth in claim 12, wherein the first and second parts are formed of Polyether ether ketone (PEEK).

14. The method as set forth in claim 13, further comprising an act of forming the scaffold by compressing a mesh tube between a scaffolding mold first part and a scaffolding mold second part, such that upon removal from the scaffolding mold first and second parts, the mesh tube resembles a tri-leaflet valve shape.

* * * * *